(12) United States Patent
Triffo

(10) Patent No.: US 9,884,184 B2
(45) Date of Patent: Feb. 6, 2018

(54) WIRE HOOK COUPLING FOR LEAD EXTENSION AND EXTRACTION

(71) Applicant: The Spectranetics Corporation, Colorado Springs, CO (US)

(72) Inventor: Thomas Kelby Triffo, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 0 days.

(21) Appl. No.: 14/954,177

(22) Filed: Nov. 30, 2015

(65) Prior Publication Data

US 2016/0184579 A1 Jun. 30, 2016

Related U.S. Application Data

(60) Provisional application No. 62/098,209, filed on Dec. 30, 2014.

(51) Int. Cl.
*A61N 1/00* (2006.01)
*A61N 1/05* (2006.01)

(52) U.S. Cl.
CPC ............ *A61N 1/056* (2013.01); *A61N 1/0587* (2013.01); *A61N 2001/0578* (2013.01)

(58) Field of Classification Search
CPC ........ A61B 17/32056; A61B 17/00234; A61B 17/50; A61B 17/221; A61B 2017/00358; A61B 2017/2212; A61B 2017/2217; A61B 2018/1407; A61B 2018/141; A61M 25/01; A61N 2001/0578; A61N 1/0587; A61N 1/372; A61N 1/056
See application file for complete search history.

(56) References Cited

U.S. PATENT DOCUMENTS 1,891,497 A 12/1932 Birkenmaier
2,446,710 A 8/1948 Makaroff
(Continued)

FOREIGN PATENT DOCUMENTS

DE 19964093 B4 11/2001
EP 169784 A2 1/1986
(Continued)

OTHER PUBLICATIONS

Smith et al. Extraction of Transvenous Pacing and ICD Leads; Pace vol. 31 Jun. 2008 pp. 736-752.

*Primary Examiner* — Scott Getzow
(74) *Attorney, Agent, or Firm* — Faegre Baker Daniels LLP

(57) ABSTRACT

A device for extending a lead according to an embodiment of the present disclosure includes a body having proximal and distal ends, the distal end having first and second apertures, the body having an inner lumen, the first and second apertures extending from an outside of the body to the inner lumen; a filamentous element extending out of the first aperture and into the second aperture to form a filament loop extending from the body; a tightening mechanism configured to twist the filamentous element to compress a lead body between the filament loop and the body; and a tether coupled to body and configured to extend further proximally than a proximal-most end of the lead body when the lead body is compressed between the filament loop and body, the tether further configured to transfer at least a portion of a tension force applied to the tether to the lead body.

20 Claims, 4 Drawing Sheets

(56) References Cited

U.S. PATENT DOCUMENTS

| | | |
|---|---|---|
| 2,615,402 A | 10/1952 | Chamberlain, Jr. |
| 2,627,137 A | 2/1953 | Koski |
| 2,856,933 A | 10/1958 | Scharf et al. |
| 3,068,608 A | 12/1962 | Counts |
| 3,220,138 A | 11/1965 | Greenfield |
| 3,955,578 A | 5/1976 | Chamness et al. |
| 4,208,827 A | 6/1980 | Starkey |
| 4,250,653 A | 2/1981 | Davies |
| 4,471,777 A | 9/1984 | McCorkle, Jr. |
| 4,506,471 A | 3/1985 | Riead |
| 4,506,472 A | 3/1985 | Barman |
| 4,582,056 A | 4/1986 | McCorkle, Jr. |
| 4,636,346 A | 1/1987 | Gold et al. |
| 4,824,435 A | 4/1989 | Giesy et al. |
| 4,943,289 A | 7/1990 | Goode et al. |
| 4,988,347 A | 1/1991 | Goode et al. |
| 5,011,482 A | 4/1991 | Goode et al. |
| 5,013,310 A | 5/1991 | Goode et al. |
| 5,036,854 A | 8/1991 | Schollmeyer et al. |
| 5,098,440 A | 3/1992 | Hillstead |
| 5,163,938 A | 11/1992 | Kambara et al. |
| 5,171,233 A | 12/1992 | Amplatz et al. |
| 5,171,314 A | 12/1992 | Dulebohn |
| 5,192,286 A | 3/1993 | Phan et al. |
| 5,207,683 A | 5/1993 | Goode et al. |
| 5,224,935 A | 7/1993 | Hollands |
| 5,247,942 A | 9/1993 | Prather et al. |
| 5,263,493 A | 11/1993 | Avitall |
| 5,282,478 A | 2/1994 | Fleischhaker et al. |
| 5,312,423 A | 5/1994 | Rosenbluth et al. |
| 5,342,371 A | 8/1994 | Welter et al. |
| 5,387,219 A | 2/1995 | Rappe |
| 5,417,684 A | 5/1995 | Jackson et al. |
| 5,443,472 A | 8/1995 | Li |
| 5,509,902 A | 4/1996 | Raulerson |
| 5,522,819 A | 6/1996 | Graves et al. |
| 5,555,883 A | 9/1996 | Avitall |
| 5,562,678 A | 10/1996 | Booker |
| 5,611,803 A | 3/1997 | Heaven et al. |
| 5,613,973 A | 3/1997 | Jackson et al. |
| 5,632,749 A | 5/1997 | Goode et al. |
| 5,637,098 A | 6/1997 | Bierman |
| 5,653,716 A | 8/1997 | Malo et al. |
| 5,681,347 A | 10/1997 | Cathcart et al. |
| 5,693,059 A | 12/1997 | Yoon |
| 5,697,936 A | 12/1997 | Shipko et al. |
| 5,769,858 A | 6/1998 | Pearson et al. |
| 5,782,839 A | 7/1998 | Hart et al. |
| 5,823,971 A | 10/1998 | Robinson et al. |
| 5,836,947 A | 11/1998 | Fleischman et al. |
| 5,868,754 A | 2/1999 | Levine et al. |
| 6,088,609 A | 7/2000 | Larison, II |
| 6,090,129 A | 7/2000 | Ouchi |
| 6,093,195 A | 7/2000 | Ouchi |
| 6,136,005 A | 10/2000 | Goode et al. |
| 6,167,315 A | 12/2000 | Coe et al. |
| 6,290,693 B1 | 9/2001 | Jung et al. |
| 6,375,639 B1 | 4/2002 | Duplessie et al. |
| 6,379,319 B1 | 4/2002 | Garibotto et al. |
| 6,432,115 B1 | 8/2002 | Mollenauer et al. |
| 6,478,777 B1 | 11/2002 | Honeck et al. |
| 6,500,182 B2 | 12/2002 | Foster |
| 6,511,492 B1 | 1/2003 | Rosenbluth et al. |
| 6,517,550 B1 | 2/2003 | Kónya et al. |
| 6,544,269 B2 | 4/2003 | Osborne et al. |
| 6,575,988 B2 | 6/2003 | Rousseau |
| 6,598,335 B2 | 7/2003 | Akhtar et al. |
| 6,687,548 B2 | 2/2004 | Goode |
| 6,695,813 B1 | 2/2004 | Boyle et al. |
| 6,712,826 B2 | 3/2004 | Lui |
| 6,743,228 B2 | 6/2004 | Lee et al. |
| 6,840,000 B2 | 1/2005 | Akhtar et al. |
| 6,893,450 B2 | 5/2005 | Foster |
| 7,041,108 B2 | 5/2006 | Lippitt et al. |
| 7,101,378 B2 | 9/2006 | Salameh et al. |
| 7,210,210 B2 | 5/2007 | Lippitt et |
| 7,359,756 B2 | 4/2008 | Goode |
| 7,470,256 B2 | 12/2008 | Lampropoulos et al. |
| 7,499,756 B2 | 3/2009 | Bowe et al. |
| 7,520,881 B2 | 4/2009 | Foushee et al. |
| 7,524,281 B2 | 4/2009 | Chu et al. |
| 7,641,646 B2 | 1/2010 | Kennedy, II |
| 7,651,503 B1 | 1/2010 | Coe et al. |
| 7,651,504 B2 | 1/2010 | Goode et al. |
| 7,713,275 B2 | 5/2010 | Greenberg et al. |
| 7,727,253 B2 | 6/2010 | Ackerman et al. |
| 7,731,693 B2 | 6/2010 | Melsheimer |
| 7,753,917 B2 | 7/2010 | Urbanski et al. |
| 7,753,918 B2 | 7/2010 | Hartley et al. |
| 7,758,592 B2 | 7/2010 | Ayala et al. |
| 7,776,052 B2 | 8/2010 | Greenberg et al. |
| 7,824,342 B2 | 11/2010 | Minosawa et al. |
| 7,871,414 B2 | 1/2011 | Hardin et al. |
| 7,993,359 B1 | 8/2011 | Atwell et al. |
| 8,070,693 B2 | 12/2011 | Ayala et al. |
| 8,109,986 B2 | 2/2012 | Styrc |
| 8,128,636 B2 | 3/2012 | Lui et al. |
| 8,137,291 B2 | 3/2012 | Melsheimer |
| 8,192,430 B2 | 6/2012 | Goode et al. |
| 8,252,019 B2 | 8/2012 | Fleming et al. |
| 8,323,179 B2 | 12/2012 | Chu et al. |
| 8,326,437 B2 | 12/2012 | Cully et al. |
| 8,469,970 B2 | 6/2013 | Diamant et al. |
| 8,551,139 B2 | 10/2013 | Surti et al. |
| 8,597,303 B2 | 12/2013 | Hammack et al. |
| 8,702,625 B2 | 4/2014 | Ayala et al. |
| 8,715,205 B2 | 5/2014 | Carter et al. |
| 8,740,969 B2 | 6/2014 | Jensen et al. |
| 8,747,295 B2 | 6/2014 | Chu et al. |
| 8,758,326 B2 | 6/2014 | Hennessy |
| 8,814,900 B2 | 8/2014 | Fleming et al. |
| 9,220,523 B2 | 12/2015 | Taylor et al. |
| 2002/0007204 A1 | 1/2002 | Goode |
| 2002/0010475 A1 | 1/2002 | Lui |
| 2002/0087100 A1 | 7/2002 | Onuki et al. |
| 2002/0107526 A1 | 8/2002 | Greenberg et al. |
| 2002/0123765 A1 | 9/2002 | Sepetka et al. |
| 2003/0187457 A1 | 10/2003 | Weber |
| 2004/0116939 A1 | 6/2004 | Goode |
| 2004/0123765 A1 | 7/2004 | Furusawa et al. |
| 2004/0153096 A1 | 8/2004 | Goode et al. |
| 2004/0199200 A1 | 10/2004 | Teague et al. |
| 2004/0220604 A1 | 11/2004 | Fogarty et al. |
| 2004/0243168 A1 | 12/2004 | Ferrera et al. |
| 2005/0043743 A1 | 2/2005 | Dennis |
| 2005/0096650 A1* | 5/2005 | Ouchi ............... A61B 18/1402 606/47 |
| 2005/0177022 A1 | 8/2005 | Chu et al. |
| 2005/0209609 A1 | 9/2005 | Wallace |
| 2006/0073904 A1 | 4/2006 | Novak |
| 2006/0100545 A1 | 5/2006 | Ayala et al. |
| 2006/0149295 A1 | 7/2006 | Fleming III |
| 2007/0123804 A1 | 5/2007 | Ayala et al. |
| 2007/0191919 A1 | 8/2007 | Lui et al. |
| 2008/0147061 A1 | 6/2008 | Goode et al. |
| 2008/0147111 A1 | 6/2008 | Johnson et al. |
| 2008/0208075 A1 | 8/2008 | Goldenberg |
| 2008/0221587 A1 | 9/2008 | Schwartz |
| 2009/0112244 A1 | 4/2009 | Freudenthal |
| 2009/0234367 A1 | 9/2009 | Verma |
| 2010/0042107 A1 | 2/2010 | Merrifield |
| 2010/0252049 A1 | 10/2010 | Kost |
| 2011/0098720 A1 | 4/2011 | Taylor et al. |
| 2011/0106099 A1 | 5/2011 | Duffy et al. |
| 2011/0106107 A1 | 5/2011 | Binmoeller et al. |
| 2011/0112548 A1 | 5/2011 | Fifer et al. |
| 2011/0238078 A1 | 9/2011 | Goode et al. |
| 2012/0165827 A1 | 6/2012 | Khairkhahan et al. |
| 2012/0165850 A1 | 6/2012 | Deckard et al. |
| 2012/0310214 A1 | 12/2012 | Hennessy |
| 2013/0006261 A1 | 1/2013 | Lampropoulos et al. |
| 2013/0006262 A1 | 1/2013 | Lampropoulos et al. |
| 2013/0131688 A1 | 5/2013 | Schwartz |
| 2013/0172714 A1 | 7/2013 | Li et al. |

(56) References Cited

U.S. PATENT DOCUMENTS

| | | |
|---|---|---|
| 2013/0184738 A1 | 7/2013 | Laroya et al. |
| 2013/0184741 A1 | 7/2013 | Laroya et al. |
| 2013/0197476 A1 | 8/2013 | Karpiel |
| 2013/0238024 A1 | 9/2013 | Taylor et al. |
| 2013/0261638 A1 | 10/2013 | Diamant et al. |
| 2014/0155930 A1 | 6/2014 | Bennett et al. |
| 2014/0171960 A1* | 6/2014 | Goode ............ A61B 17/00 606/129 |
| 2014/0188124 A1 | 7/2014 | Lampropoulos et al. |
| 2014/0296905 A1 | 10/2014 | Dela |
| 2014/0350566 A1 | 11/2014 | Emmanouilidis |
| 2014/0350593 A1 | 11/2014 | Laroya et al. |
| 2016/0183954 A1 | 6/2016 | Taylor et al. |
| 2016/0184576 A1 | 6/2016 | Grace et al. |
| 2016/0184580 A1* | 6/2016 | Grace ............ A61N 1/056 607/119 |

FOREIGN PATENT DOCUMENTS

| | | |
|---|---|---|
| EP | 3174930 A1 | 3/1986 |
| EP | 3368568 B1 | 5/1990 |
| EP | 3661949 A1 | 7/1995 |
| EP | 3688184 A1 | 12/1995 |
| EP | 3708621 B1 | 5/1996 |
| EP | 3733382 A2 | 9/1996 |
| EP | 3733383 A2 | 9/1996 |
| EP | 1043042 B1 | 10/2000 |
| EP | 1063926 B1 | 1/2001 |
| EP | 1251787 B1 | 10/2002 |
| EP | 1284782 B1 | 2/2003 |
| EP | 1317214 B1 | 6/2003 |
| EP | 1330194 B1 | 7/2003 |
| EP | 1572282 B1 | 9/2005 |
| EP | 1587573 B1 | 10/2005 |
| EP | 1722696 A1 | 11/2006 |
| EP | 1757234 B1 | 2/2007 |
| EP | 1793886 B1 | 6/2007 |
| EP | 1815811 B1 | 8/2007 |
| EP | 1848497 B1 | 10/2007 |
| EP | 1951350 B1 | 8/2008 |
| EP | 1984056 A1 | 10/2008 |
| EP | 1984072 A2 | 10/2008 |
| EP | 1996089 B1 | 12/2008 |
| EP | 2054116 B1 | 5/2009 |
| EP | 2094178 B1 | 9/2009 |
| EP | 2124766 B1 | 12/2009 |
| EP | 2240126 B1 | 10/2010 |
| EP | 2349026 B1 | 8/2011 |
| EP | 2375997 B1 | 10/2011 |
| EP | 2489313 A1 | 8/2012 |
| EP | 2493392 B1 | 9/2012 |
| EP | 2496151 A2 | 9/2012 |
| EP | 2552327 A1 | 2/2013 |
| EP | 2659841 A2 | 11/2013 |
| EP | 2661233 A1 | 11/2013 |
| EP | 2661288 A1 | 11/2013 |
| EP | 2731513 A1 | 5/2014 |
| EP | 2740437 A1 | 6/2014 |
| EP | 2742871 B1 | 6/2014 |
| EP | 2783658 A2 | 10/2014 |
| EP | 2802276 A1 | 11/2014 |
| WO | 1996028101 A1 | 9/1996 |
| WO | 2001056484 A1 | 8/2001 |
| WO | 2001087412 A2 | 11/2001 |
| WO | 2002022028 A2 | 3/2002 |
| WO | 2005084563 A1 | 9/2005 |
| WO | 2007095252 A1 | 8/2007 |
| WO | 2007100474 A2 | 9/2007 |
| WO | 2008045143 A2 | 4/2008 |
| WO | 2008112608 A2 | 9/2008 |
| WO | 2010002549 A2 | 1/2010 |
| WO | 2011032157 A1 | 3/2011 |
| WO | 2011053645 A1 | 5/2011 |
| WO | 2011123342 A1 | 10/2011 |
| WO | 2012006247 A1 | 1/2012 |
| WO | 2013106713 A1 | 7/2013 |
| WO | 2014080338 A1 | 5/2014 |
| WO | 2014145598 A1 | 9/2014 |

* cited by examiner

WIRE HOOK COUPLING FOR LEAD EXTENSION AND EXTRACTION

CROSS-REFERENCE TO RELATED APPLICATION

The present application claims the benefit of and priority to, under 35 U.S.C. § 119(e), U.S. Provisional Application Ser. No. 62/098,209, filed Dec. 30, 2014, entitled WIRE HOOK COUPLING FOR LEAD EXTENSION AND EXTRACTION, which is hereby incorporated by reference in its entirety for all purposes.

FIELD OF THE DISCLOSURE

The present disclosure relates generally to lead extension and extraction, and more specifically to methods and devices for extending a lead to lengthen a guide structure over which a lead extraction device may be passed.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter-defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure every 5 to 10 years. Another part of the system includes the wires, or leads, which run between the pulse generator and the heart. In a pacemaker, these leads allow the device to increase the heart rate by delivering small timed bursts of electric energy to make the heart beat according to a healthy rhythm. In a defibrillator, the lead has special coils to allow the device to deliver a high-energy shock and convert potentially dangerous rapid rhythms (ventricular tachycardia or fibrillation) back to a normal rhythm. Additionally, the leads may transmit information about the heart's electrical activity to the pacemaker.

For both of these functions, leads must be in contact with heart tissue. Most leads pass through a vein under the collarbone that connects to the right side of the heart (right atrium and right ventricle). In some cases, a lead is inserted through a vein and guided into a heart chamber where it is attached with the heart. In other instances, a lead is attached to the outside of the heart. To remain attached to the heart muscle, most leads have a fixation mechanism, such as a small screw and/or hooks at the end.

Within a relatively short time after a lead is implanted into the body, the body's natural healing process forms scar tissue along the lead and possibly at its tip, thereby fastening it even more securely in the patient's body. Leads usually last longer than device batteries, so leads are simply reconnected to each new pulse generator (battery) at the time of replacement. Although leads are designed to be implanted permanently in the body, occasionally these leads must be removed, or extracted. Leads may be removed from patients for numerous reasons, including but not limited to, infections, lead age, and lead malfunction.

Removal or extraction of the lead may be difficult. The body's natural healing process forms scar tissue over and along the lead, and possibly at its tip, thereby encasing at least a portion of the lead and fastening it even more securely in the patient's body. In addition, the lead and/or tissue may become attached to the vasculature wall. Both results may, therefore, increase the difficulty of removing the leads from the patient's vasculature. Typical leads in a human may pass through the innominate vein, past the superior vena cava ("SVC"), and into the right atrium of the heart. Tissue growth occurring along the SVC and other locations along the innominate vein may increase the risk and difficulty in extracting the leads from such locations, particularly when the vein(s)' walls are thin and the surrounding tissue is notably fibrous.

A variety of tools have been developed to make lead extraction safer and more successful. Current lead extraction techniques include mechanical traction, mechanical devices, and laser devices. Extracting a lead may often involve applying tension to the lead while it is still implanted, whether in order to pull it free using the tension force, to loosen it, and/or to apply an extraction device over the lead. Applying an extraction device over a lead which is not adequately tensioned may result in kinking or damage to the lead, for example at locations which are not as easy to access as the proximal portion of the lead that was near to or coupled with the pacemaker or defibrillator. In extracting a lead, the lead (including any conductive portions, insulating sheath, and/or casing layers) is often cut between the distal end of the lead and the proximal end of the lead (which is often coupled to the pacemaker). In other situations, the lead exhibits structural failure, either before, or during, the lead extraction surgical intervention. These situations may result in a lead that is not as long as the clinician would like it to be in order to both apply tension to the lead and/or deploy an extraction device over the lead. Existing lead extension technologies may be limited in the maximum level of tension which they can support in coupling with the lead, with the reversibility of such coupling, and/or with the reliability of such coupling.

SUMMARY

A device for extending a lead according to an embodiment of the present disclosure includes a body having a proximal end and a distal end, the distal end having a first aperture and a second aperture, the body having an inner lumen, the first and second apertures extending from an outside of the body to the inner lumen; a filamentous element extending through the inner lumen, out of the first aperture, and into the second aperture to form a filament loop extending from the body; a tightening mechanism operatively coupled to the body, the tightening mechanism configured to twist the filamentous element to compress a lead body between the filament loop and the body; and a tether coupled to body, the tether configured to extend further proximally than a proximal-most end of the lead body when the lead body is compressed between the filament loop and the body, the tether further configured to transfer at least a portion of a tension force applied to the tether to the lead body.

In some embodiments, the body further includes third and fourth apertures extending from the outside of the body to the inner lumen. A raised ledge may be formed on the outside of the body, the raised ledge extending between the first and second apertures and/or between the third and fourth apertures, if any.

In some cases, the tightening mechanism includes a first aperture and a second aperture, wherein the filamentous element extends through the first aperture of the tightening mechanism before extending out of the first aperture of the body, and into the second aperture of the body, and then through the second aperture of the tightening mechanism. The tightening mechanism may be an end cap coupled to the proximal end of the body, the end cap rotatable about a central axis of the inner lumen, such that rotation of the end cap twists the filamentous element between the end cap and the distal end of the body. The end cap may include an inner lip, the proximal end of the body may include an outer groove, and the end cap may couple to the body by press fitting the inner lip into the outer groove, according to some embodiments.

In some instances, the filament loop is a first filament loop and the filamentous element is a first filamentous element, the device further including a second filament looped formed by a second filamentous element that extends through the inner lumen, out of the third aperture, and into the fourth aperture to form the second filament loop extending from the body. According to some embodiments, the tightening mechanism is an end cap coupled to the proximal end of the body, the end cap includes a first aperture, a second aperture, a third aperture, and a fourth aperture, and the first filamentous element extends through the first and second apertures of the end cap and the second filamentous element extends through the third and fourth apertures of the end cap, the end cap rotatable about a central axis of the inner lumen, such that rotation of the end cap twists the first and second filamentous elements between the end cap and the distal end of the body.

A method for extending a lead according to an embodiment of the present disclosure includes placing a lead through a filament loop, the filament loop formed of a filamentous element extending through an inner lumen of a body, out of a first aperture formed through a distal end of the body between the inner lumen and an outer surface of the body, and back through a second aperture formed through the distal end of the body between the inner lumen and the outer surface of the body, and back through the inner lumen of the body; tightening the filament loop by pulling each free end of the filamentous element proximally through the inner lumen; further tightening the filament loop by twisting the filamentous element within the inner lumen between the proximal and distal ends of the body to compress the lead against the outer surface of the body with the filament loop; and applying tension to the lead by applying tension to a tether that is coupled to the lead via the body when the filament loop is tightened about the lead.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

A "lead" is a conductive structure, typically an electrically insulated coiled wire. The electrically conductive material may be any conductive material, with metals and intermetallic alloys common. The outer sheath of insulated material is biocompatible and bio stable (e.g., non-dissolving in the body) and generally includes organic materials such as polyurethane and polyimide. Lead types include, by way of non-limiting example, epicardial and endocardial leads. Leads are commonly implanted into a body percutaneously or surgically.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate possible and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
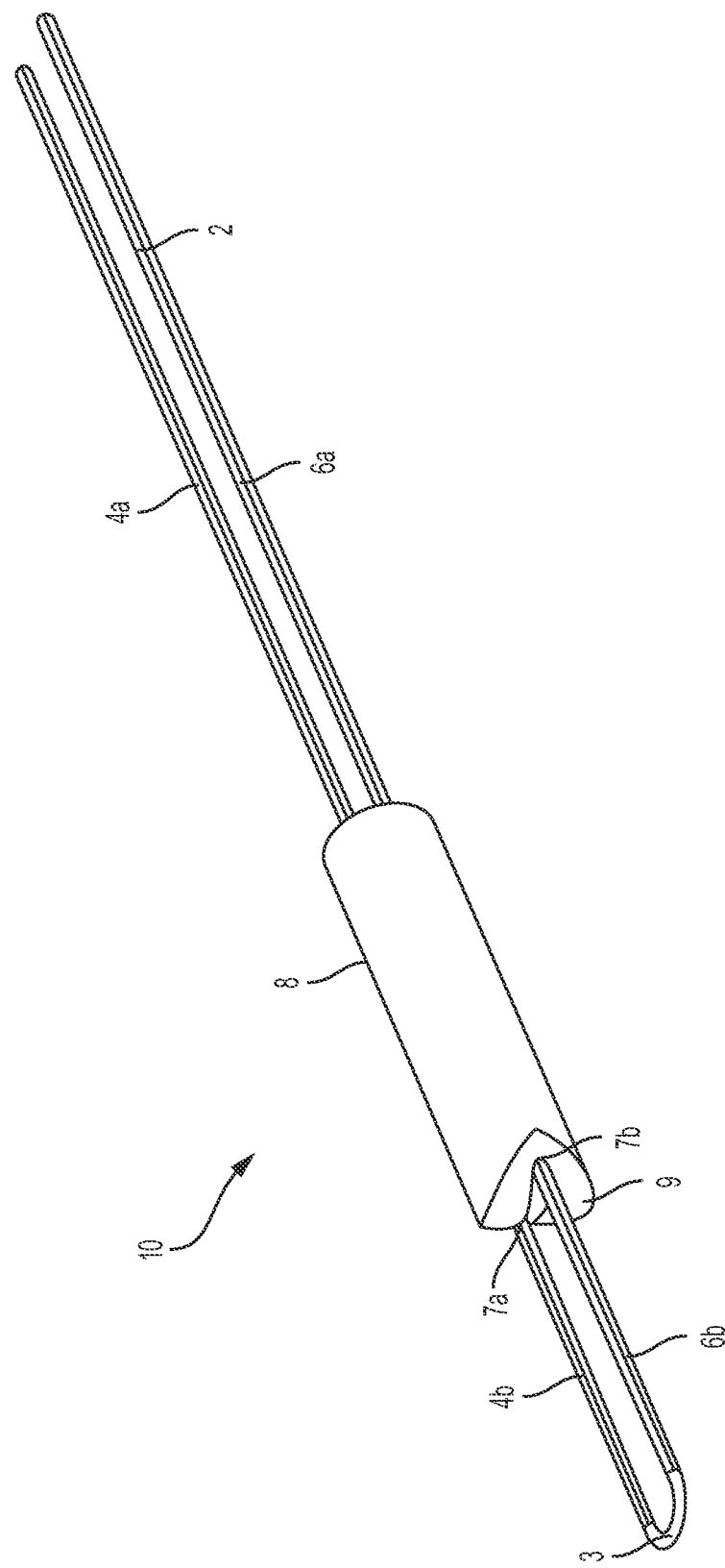
FIG. 1 illustrates a top and front perspective view of a lead extension device, according to an embodiment of the present disclosure.

FIG. 1 illustrates a top and front perspective view of a lead extension device 10, according to an embodiment of the present disclosure. Device 10 includes a body 8, with a filament or filamentous element 2, such as a wire, suture, or other elongated structure extending through the body 8. Filament 2 includes different portions, for example portion 4a extends from a proximal end toward a proximal end of the body 8, through the body 8, through aperture 7a, where it extends from the body 8 as section 4b. Then filament 2 becomes a looped end 3, then portion 6b before it goes back into body 8 through aperture 7b, back through body 8, and extending back toward a proximal direction along portion 6a. A lead or lead portion or other elongated element may be inserted through the filament loop 3, and then the filament loop 3 may be closed, for example by pulling end portions 4a, 6a proximally with respect to the body 8 to compress the lead against the distal face 9 of the body 8 with loop 3.

Filamentous element 2 may be, for example, a stainless steel wire passing through a cylindrical housing 8. In some embodiments, the cylindrical housing 8 allows the wire 2 to pass through, but acts as a hard stop against which the wire loop 3 can be used to pull lead components against. In the opening of the loop 3 the lead components (lead body insulation, high voltage cables, and/or the like) are inserted, then the wire ends (e.g. 4a, 6a) are pulled taut to secure the lead components against the cylinder 8. To lock the components in place the trailing wire segments 4a, 6a are twisted together. The tighter these wires 4a, 6a are joined, the greater the compressive force exerted on the lead.

Figure 2:
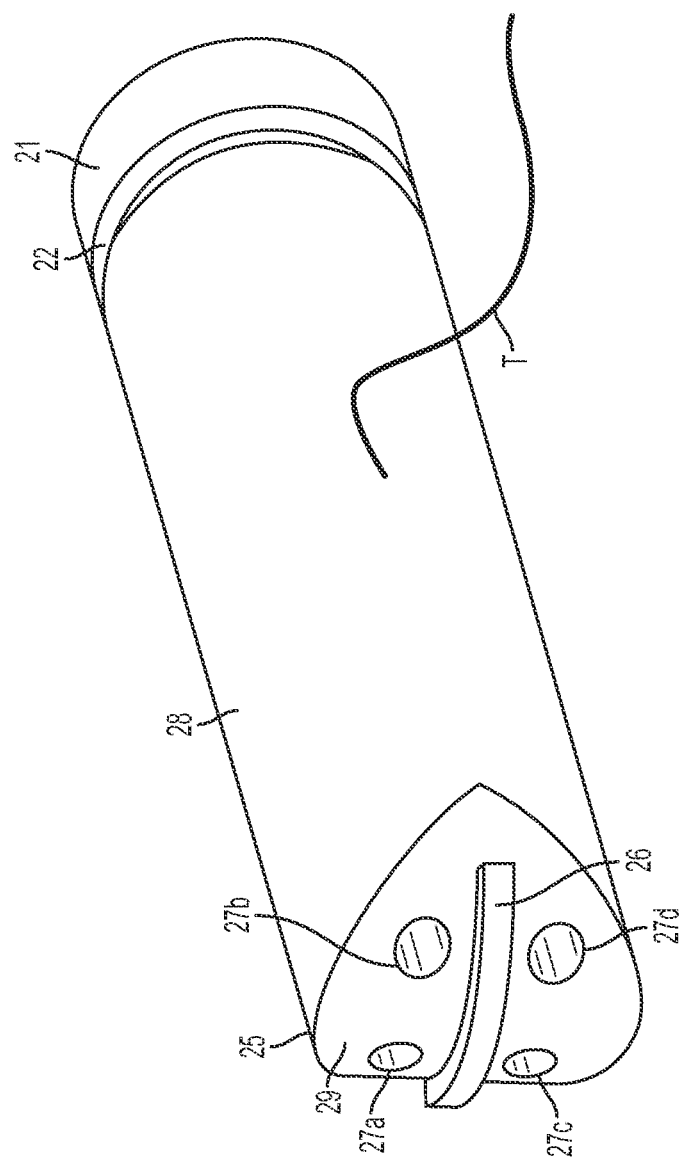
FIG. 2 illustrates an enlarged top and front perspective view of a body for a lead extension device, according to an embodiment of the present disclosure.

FIG. 2 illustrates an enlarged top and front perspective view of a body 28 for a lead extension device, according to an embodiment of the present disclosure. Body 28 may be similar to body 8, in some cases. Body 28 may include four apertures 27a, 27b, 27c, 27d at its distal end 25, along face 29. A filament 2 may be placed through two of the four apertures 27 in the manner shown in FIG. 1, and another filament may be placed through another two of the four apertures 27 in the same manner, according to some embodiments.

The distal face 29 may include a raised ridge 26, for example between hole 27a and 27c and between hole 27b and 27d. Raised ridge 26 protrudes above an outer extent of distal surface 29; in this manner, a filament loop 3 formed by a filament 2 with each of its ends extending through holes 27a and 27b may be used to capture one portion of a lead extending through the filament loop 3, and another filament loop 3 formed by a filament 2 with each of its end extending through holes 27c and 27d may be used to capture another portion of the lead extending through the filament loop 3. When both the top and bottom filament loops are tightened, the lead is compressed against distal face 29 both above and below the raised ridge 26, which operates to form a three-point bend in the lead. This three-point bend improves the effectiveness with which such loops 3 can grip the lead against the body 28 by creating a circuitous deformation of the lead, making it more difficult for the lead to escape from the body 28 and loops 3 when the loops 3 are tightened against the distal face 29.

Figure 3:
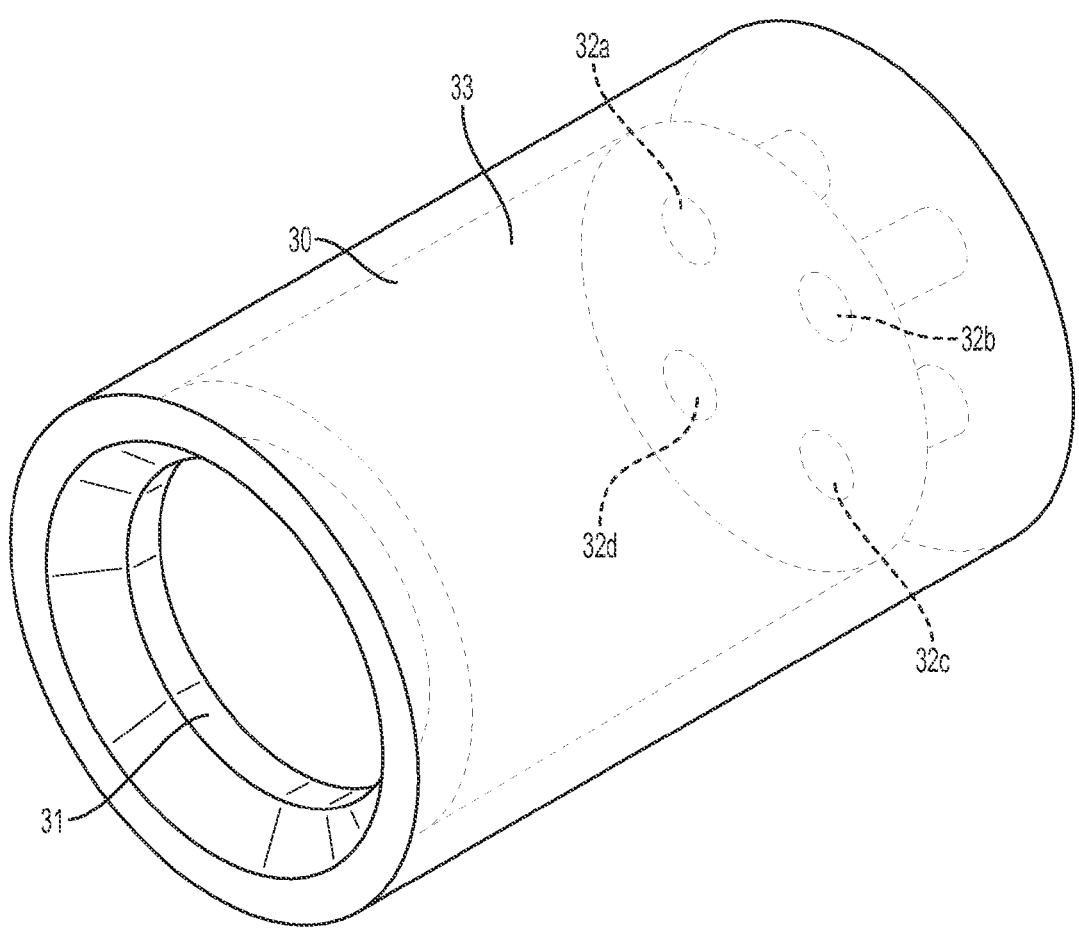
FIG. 3 illustrates a partially transparent top and front perspective view of a tightening mechanism/end cap according to an embodiment of the present disclosure.
Figure 4:
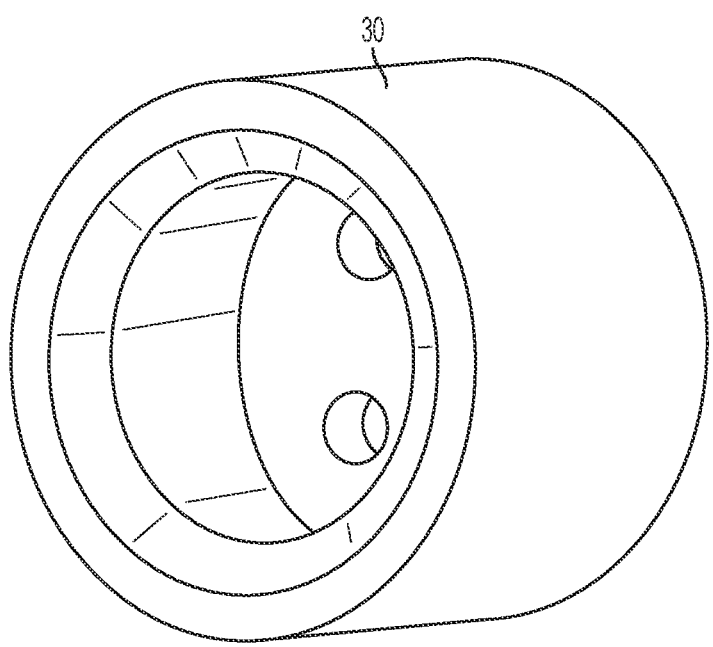
FIG. 4 illustrates a top and front perspective view of the tightening mechanism of FIG. 3, according to an embodiment of the present disclosure.

FIGS. 3 and 4 illustrate a tightening mechanism/end cap 30 according to an embodiment of the present disclosure. The tightening mechanism 30 includes a distal raised lip 31 along all or part of its inner surface or circumference. This raised lip 31 may be inserted over and/or press fit into a channel 22 formed at or near the proximal end 21 of the body 28 (see FIG. 2). When two filament loops are used with body 28, each end of the two filament loops may be extended further not only through apertures 27 in the distal end 25 of body 28, but may further each be extended through apertures 32a, 32b, 32c, and 32d formed in tightening mechanism 30. When the tightening mechanism 30 is coupled with body 28, for example via raised lip 31 interfacing with channel 22, or other interlocking mechanism, the tightening mechanism 30 may rotate about a central axis of the body 28 and/or end cap 31. After the loops extending out of distal face 29 have been tightened, for example by pulling the wires proximally, the loops may be further tightened, and/or locked in place, by twisting the tightening mechanism 30. This will have the effect of twisting the wire(s) within body 28, thereby further tightening the loops through which the captured lead passes, and/or preventing loosening of the loops due to the twists inside the body 28. This tightening and/or locking may be reversible in some cases, for example by turning the tightening mechanism in an opposite direction.

A tether T may be coupled with the body 28 (and/or body 8) and/or with filamentous element 2, such that the tether T extends proximally further than the captured lead extended or was able to extend. The tether T may be tensioned proximally in order to transfer such tension to the body 28 and thus the lead(s) captured within loops 3. The tether T may further serve to receive a lead extraction device thereover in order to move such device distally until it reaches the captured lead for further extraction of the captured lead, according to some embodiments.

Increasing the number of through channels 27 in the cylinder 28 (as compared, for example, to the through channels 7 in cylinder 8) increases the number of wires 2 that can be used, allowing for the creation of various patterns of wires 2 to be used to secure the lead components. According to some embodiments, the raised ridge 26 between the sets (27a, 27b and 27c, 27d) of holes will push up on lead components, in opposition to the wire loops 3 that are pulling down on the lead components. This counter force will allow for a more secure lock on the lead components by placing them into a three point bend. At the rear 21 of the device 28 is a recessed channel 22, which can be used in conjunction with the piece 30 shown in FIGS. 3 and 4.

As described above, the end cap 30 has a raised lip 31 on the inner surface, which can be press fit and mated into the recessed channel 22 on the proximal end 21 of body 28. The wires 2 pass through the cap channels 32, then once the cap 30 is pressed into place it can be rotated to twist the wires 2 and lock the device. This results in a simple mechanism through which the physician can lock the device, according to embodiments of the present disclosure. To improve the ability to twist the device, the outer surface 33 of the end cap 30 could be roughened through a variety of mechanisms, for example roughening, knurling, high friction coating, and other mechanisms.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

A number of variations and modifications of the disclosure may be used. It would be possible to provide for some features of the disclosure without providing others.

The present disclosure, in various aspects, embodiments, and/or configurations, includes components, methods, processes, systems and/or apparatus substantially as depicted and described herein, including various aspects, embodiments, configurations embodiments, sub combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Summary, with each claim standing on its own as a separate embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device for extending a lead, comprising:
   a body having a proximal end and a distal end, the distal end having a first aperture and a second aperture, the body having an inner lumen, the first and second apertures extending from an outside of the body to the inner lumen;
   a filamentous element extending through the inner lumen, out of the first aperture, and into the second aperture to form a filament loop extending from the body;
   a tightening mechanism operatively coupled to the body, the tightening mechanism configured to twist the filamentous element to compress a lead body between the filament loop and the body; and
   a tether coupled to the body, the tether configured to extend further proximally than a proximal-most end of the lead body when the lead body is compressed between the filament loop and the body, the tether further configured to transfer at least a portion of a tension force applied to the tether to the lead body.

2. The device of claim 1, wherein the body further comprises third and fourth apertures extending from the outside of the body to the inner lumen.

3. The device of claim 2, further comprising a raised ledge formed on the outside of the body, the raised ledge extending between the first and second apertures and between the third and fourth apertures.

4. The device of claim 1, further comprising a raised ledge formed on the outside of the body, the raised ledge extending between the first and second apertures.

5. The device of claim 1, wherein the tightening mechanism comprises a first aperture and a second aperture, wherein the filamentous element extends through the first aperture of the tightening mechanism before extending out of the first aperture of the body, and into the second aperture of the body, and then through the second aperture of the tightening mechanism.

6. The device of claim 5, wherein the tightening mechanism is an end cap coupled to the proximal end of the body, the end cap rotatable about a central axis of the inner lumen, such that rotation of the end cap twists the filamentous element between the end cap and the distal end of the body.

7. The device of claim 6, wherein the end cap comprises an inner lip, wherein the proximal end of the body comprises an outer groove, and wherein the end cap couples to the body by press fitting the inner lip into the outer groove.

8. The device of claim 2, wherein the filament loop is a first filament loop and the filamentous element is a first filamentous element, the device further comprising a second filament loop formed by a second filamentous element that extends through the inner lumen, out of the third aperture, and into the fourth aperture to form the second filament loop extending from the body.

9. The device of claim 8, wherein the tightening mechanism is an end cap coupled to the proximal end of the body, the end cap comprising a first aperture, a second aperture, a third aperture, and a fourth aperture, wherein the first filamentous element extends through the first and second apertures of the end cap and the second filamentous element extends through the third and fourth apertures of the end cap, the end cap rotatable about a central axis of the inner lumen, such that rotation of the end cap twists the first and second filamentous elements between the end cap and the distal end of the body.

10. A method for extending a lead, comprising:
placing a lead through a filament loop, the filament loop formed of a filamentous element extending through an inner lumen of a body, out of a first aperture formed through a distal end of the body between the inner lumen and an outer surface of the body, and back through a second aperture formed through the distal end of the body between the inner lumen and the outer surface of the body, and back through the inner lumen of the body;
tightening the filament loop by pulling each free end of the filamentous element proximally through the inner lumen;
further tightening the filament loop by twisting the filamentous element within the inner lumen between the proximal and distal ends of the body to compress the lead against the outer surface of the body with the filament loop; and
applying tension to the lead by applying tension to a tether that is coupled to the lead via the body when the filament loop is tightened about the lead.

11. The method of claim 10, wherein at least one of tightening the filament loop and further tightening the filament loop includes compressing the lead, via the filament loop, against a raised ledge formed on the outside of the body and extending between the first and second apertures.

12. The method of claim 11, wherein further tightening the filament loop includes manipulating a tightening mechanism coupled to the body to twist the filamentous element within the inner lumen between the proximal and distal ends of the body to compress the lead against the raised ledge of the body with the filament loop.

13. The method of claim 10, wherein further tightening the filament loop includes manipulating a tightening mechanism coupled to the body to twist the filamentous element within the inner lumen between the proximal and distal ends of the body to compress the lead against the outer surface of the body with the filament loop.

14. The method of claim 13, wherein the tightening mechanism is an end cap coupled to the proximal end of the body, and further tightening the filament loop includes rotating the end cap about a central axis of the inner lumen to twist the filamentous element within the inner lumen between the proximal and distal ends of the body to compress the lead against the outer surface of the body with the filament loop.

15. The method of claim 10, wherein the filament loop is a first filament loop and the filamentous element is a first filamentous element, and further comprising:
placing the lead through a second filament loop, the second filament loop formed by a second filamentous element extending through the inner lumen of the body, out of a third aperture formed through the distal end of the body between the inner lumen and the outer surface of the body, and back through a fourth aperture formed through the distal end of the body between the inner lumen and the outer surface of the body, and back through the inner lumen of the body;
tightening the second filament loop by pulling each free end of the second filamentous element proximally through the inner lumen; and
further tightening the second filament loop by twisting the second filamentous element within the inner lumen between the proximal and distal ends of the body to compress the lead against the outer surface of the body with the second filament loop.

16. The method of claim 15, wherein at least one of tightening the first filament loop, tightening the second filament loop, further tightening the first filament loop, and further tightening the second filament loop includes compressing the lead against a raised ledge formed on the outside of the body and extending between the first and second apertures and between the third and fourth apertures.

17. The method of claim 16, wherein further tightening the first filament loop and further tightening the second filament loop includes manipulating a tightening mechanism coupled to the body to twist the first filamentous element and the second filamentous element within the inner lumen between the proximal and distal ends of the body to compress the lead against the outer surface of the body with the first filament loop and the second filament loop.

18. The method of claim 17, wherein the tightening mechanism is an end cap coupled to the proximal end of the body, and further tightening the first filament loop and further tightening the second filament loop includes rotating the end cap about a central axis of the inner lumen to twist the first filamentous element and the second filamentous element within the inner lumen between the proximal and distal ends of the body to compress the lead against the outer surface of the body with the first filament loop and the second filament loop.

19. The method of claim 15, wherein further tightening the first filament loop and further tightening the second filament loop includes manipulating a tightening mechanism coupled to the body to twist the first filamentous element and the second filamentous element within the inner lumen between the proximal and distal ends of the body to compress the lead against the outer surface of the body with the first filament loop and the second filament loop.

20. The method of claim 19, wherein the tightening mechanism is an end cap coupled to the proximal end of the body, and further tightening the first filament loop and further tightening the second filament loop includes rotating the end cap about a central axis of the inner lumen to twist the first filamentous element and the second filamentous element within the inner lumen between the proximal and distal ends of the body to compress the lead against the outer surface of the body with the first filament loop and the second filament loop.

* * * * *

UNITED STATES PATENT AND TRADEMARK OFFICE
CERTIFICATE OF CORRECTION

PATENT NO.         : 9,884,184 B2
APPLICATION NO.    : 14/954177
DATED              : February 6, 2018
INVENTOR(S)        : Triffo Page 1 of 1

It is certified that error appears in the above-identified patent and that said Letters Patent is hereby corrected as shown below:

In Column 6, Lines 41-42, delete "end cap 31." and insert -- end cap 30. --, therefor.

In Column 7, Line 5, delete "rear 21" and insert -- proximal end 21 --, therefor.

In Column 7, Line 6, delete "device 28" and insert -- body 28 --, therefor.

Signed and Sealed this
First Day of May, 2018

Andrei Iancu
*Director of the United States Patent and Trademark Office*